(12) United States Patent
Trabanino et al.

(10) Patent No.: US 8,370,074 B2
(45) Date of Patent: Feb. 5, 2013

(54) SYSTEM AND METHODS FOR PREDICTING TRANSMEMBRANE DOMAINS IN MEMBRANE PROTEINS AND MINING THE GENOME FOR RECOGNIZING G-PROTEIN COUPLED RECEPTORS

(75) Inventors: Rene J. Trabanino, Los Angeles, CA (US); Nagarajan Vaidehi, Arcadia, CA (US); Spencer E. Hall, Tucson, AZ (US); William A. Goddard, Pasadena, CA (US); Wely Floriano, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/606,605

(22) Filed: Oct. 27, 2009

(65) Prior Publication Data

US 2010/0299127 A1 Nov. 25, 2010

Related U.S. Application Data

(63) Continuation of application No. 10/901,576, filed on Jul. 29, 2004, now abandoned.

(60) Provisional application No. 60/491,334, filed on Jul. 29, 2003.

(51) Int. Cl.
*G01N 33/48* (2006.01)
*C12Q 1/68* (2006.01)
*G06G 7/58* (2006.01)
*G06F 7/60* (2006.01)

(52) U.S. Cl. .................... 702/19; 435/6; 702/20; 703/2; 703/11; 700/90

(58) Field of Classification Search .................... None
See application file for complete search history.

(56) References Cited

U.S. PATENT DOCUMENTS

| 5,940,307 | A | 8/1999 | Fischbarg et al. |
| 6,269,312 | B1 | 7/2001 | Mayo et al. |
| 2002/0099506 | A1 | 7/2002 | Floriano et al. |

FOREIGN PATENT DOCUMENTS
WO    WO-0171347 A1    9/2001

OTHER PUBLICATIONS

Datta et al., "A Designed Phenylalanyl-tRNA Synthetase Variant Allows Efficient In Vivo Incorporation of Aryl Ketone Functionality into Proteins," *J. Am. Chem. Soc.*, 124:5652-5653 (2002).
Datta et al., "Mechanism for antibody catalysis of the oxidation of water by singlet dioxygen," *Proc. Natl. Acad. Sci. USA*, 99:2636-2641 (2002).
Datta et al., "Interaction of *E. coli* outer-membrane protein A with sugars on the receptors of the brain microvascular endothelial cells," *Proteins*, 50(2):213-221 (2003).
Dombi et al., "Analysis of protein transmembrane helical regions by a neural network," *Protein Science*, 3:557-566 (1994).
Eisenberg et al., "The hydrophobic moment detects periodicity in protein hydrophobicity," *Proc. Natl. Acad. Sci. USA*, 81:140-144 (1984).
Eisenberg, "Three Dimensional Structure of Membrane and Surface Proteins," *Ann. Rev. Biochem.*, 53:595-623 (1984).
Floriano et al., "Molecular mechanisms underlying differential odor responses of a mouse olfactory receptor," *Proc. Natl. Acad. Sci. USA*, 97:10712-10716 (2000).
Flower, "Modelling G-Protein-Coupled Receptors for Drug Design," *Biochimica et Biophysica Acta*, 1422(3):207-234 (1999).
Frimurer et al., "Structure of the integral membrane domain of the GLP1 receptor," *Proteins: Structure, Function, and Genetics*, 35(4):375-386 (1999).
Halperin et al., "Principals of Docking: An Overview of Search Algorithms and a Guide to Scoring Functions," *Proteins*, 47:409-443 (2002).
Han et al., "User-Friendly and Versatile Software for Analysis of Protein Hydrophobicity," *Biotechniques*, 25(2):256-259 (1998).
Huang et al., "Ab Initio Fold Prediction of Small Helical Proteins Using Distance Geometry and Knowledge-Based Scoring Functions," *J. Mol. Biol.*, 290:267-281 (1999).
Jacobson et al., "A-3-adenosine receptors: Design of selective ligands and therapeutic prospects," *Drugs of the Future*, 20(7):689-699 (1995).
Juretic et al., "Conformational Preference Functions for Predicting Helices in Membrane Proteins," *Biopolymers*, 33:255-273 (1993).
Karlin et al., "Applications and statistics for multiple high-scoring segments in molecular sequences," *Proc. Natl. Acad. Sci. USA*, 90:5873-5877 (1993).
Lee, "$Ca^{2+}$-ATPase structure in the E1 and E2 conformations: mechanism, helix-helix and helix-lipid interactions," *Biochimica et Biophysica Acta—Biomembranes*, 1565(2):246-266 (2002).
Palczewski et al., "Crystal Structure of Rhodopsin: A G Protein-Coupled Receptor," *Science*, 289:739-745 (2000).
Phoenix et al., "The Prediction of Amphiphilic Alpha-Helices," *Current Prot. Pep. Sci.*, 3(2):201-221 (2002).
Sansom and Davison, "Modeling Transmembrane Helix Bundles by Restrained MD Simulations," *Methods Mol. Biol.*, 143:325-347 (2000).
Trabanino et al., "First Principles Predictions of the Structure and Function of G-Protein-Coupled Receptors: Validation for Bovine Rhodopsin," *Biophys. J.*, 86:1904-1921 (2004).

(Continued)

*Primary Examiner* — Eric S Dejong
(74) *Attorney, Agent, or Firm* — McCarter & English, LLP; Elizabeth A. Hanley; Yu Lu

(57) ABSTRACT

The invention provides computer-implemented methods and apparatus implementing a hierarchical protocol using multi-scale molecular dynamics and molecular modeling methods to predict the presence of transmembrane regions in proteins, such as G-Protein Coupled Receptors (GPCR), and protein structural models generated according to the protocol. The protocol features a coarse grain sampling method, such as hydrophobicity analysis, to provide a fast and accurate procedure for predicting transmembrane regions. Methods and apparatus of the invention are useful to screen protein or polynucleotide databases for encoded proteins with transmembrane regions, such as GPCRs.

15 Claims, 6 Drawing Sheets

OTHER PUBLICATIONS

Uechi et al., "An Automated Structure Prediction System by Lattice Model for Seven-Helix-Type Membrane Proteins." Poster abstract published in *Genome Informatics 1999*, eds. Asai et al., Universal Academy Press, Tokyo (1999).

Vaidehi et al., "Prediction of structure and function of G protein-coupled receptors," *Proc. Natl. Acad. Sci. USA*, 99(20):12622-12627 (2002).

Wang et al., "Virtual Screening for Binding of Phenylalanine Analogues to Phenylalanyl-tRNA Synthetase," *J. Am. Chem. Soc.*, 124(48):14442-14449 (2002).

Merriam-Webster Dictionary definition for the term, "device," printed online from <http://www.merriam-webster.com/cgi-bin/dictionary?book=Dictionary&va=device> on Aug. 12, 2008.

NCBI webstie: Statistics of Sequence Similarity Score, printed from <http://74.125.45.132/search?q=cache:kO5rAZG_41EJ:www.ncbi.nlm.nih.gov/BLAST/tutorial/Altschul-1.html> on Aug. 24, 2008.

Fig. 1
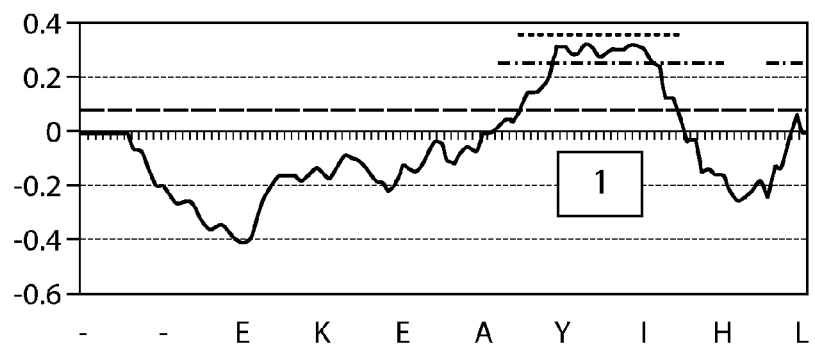
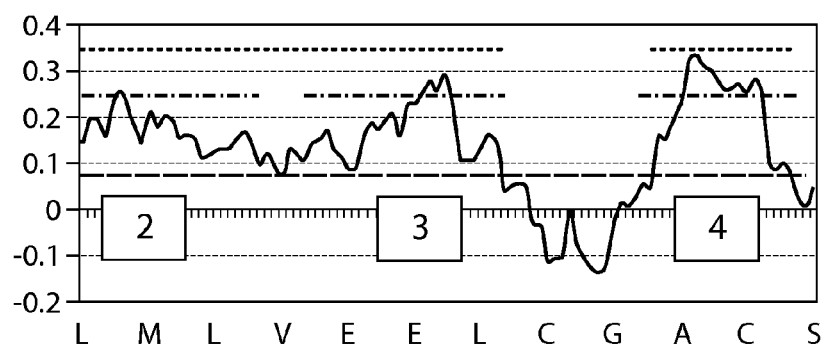
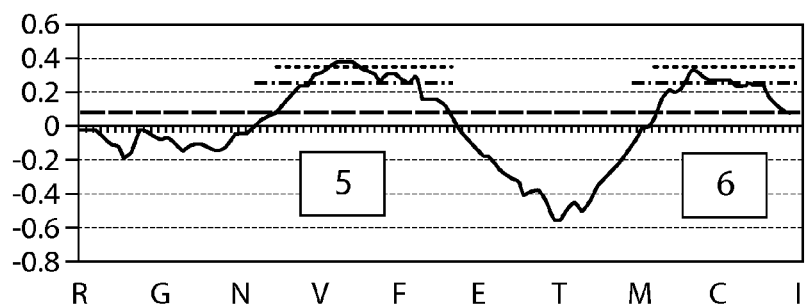
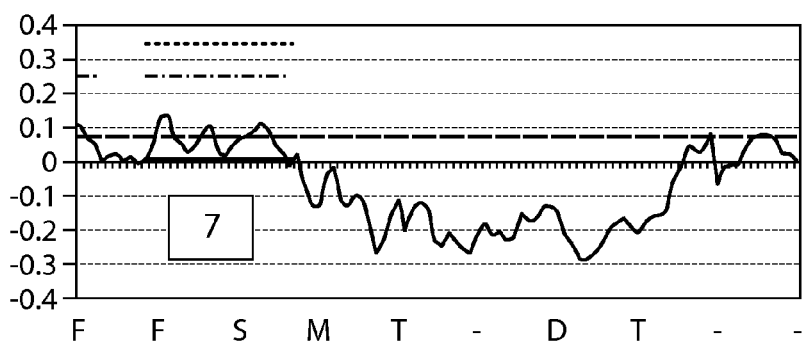

Fig. 2

|  |  | Size | Range |
|---|---|---|---|
| TM1: | | | |
| FSMLAAYMFLLIMLGFPINFLTL | Before capping | 23 | 37-59 |
| PWQFSMLAAYMFLLIMLGFPINFLTLYVTVQH | After capping | 32 | 34-65 |
| WQFSMLAAYMFLLIMLGFPINFLTLYVTVQ | Crystal | 30 | 35-64 |
| TM2: | | | |
| LNLAVADLFMVFGGFTTTLYTSLHGYFV | Before capping | 28 | 77-104 |
| PLNYILLNLAVADLFMVFGGFTTTLYTSLHG | After capping | 31 | 71-101 |
| PLNYILLNLAVADLFMVFgGFTtTLYTSLh | Crystal | 30 | 71-100 |
| TM3: | | | |
| VFGPTGCNLEGFFATLGGEIALWSLVVLAIE | Before capping | 31 | 104-134 |
| PTGCNLEGFFATLGGEIALWSLVVLAIE | After capping | 28 | 107-134 |
| PTGCNLEGFFATLGGEIALWSLvVLAIERYvvV | Crystal | 33 | 107-139 |
| TM4: | | | |
| IMGVAFTWVMALACAAPPLV | Before capping | 20 | 154-173 |
| HAIMGVAFTWVMALACAAPPLVG | After capping | 23 | 152-174 |
| NHAIMGVAFTWVmaLacAAPPLV | Crystal | 23 | 151-173 |
| TM5: | | | |
| VIYMFVVHFIIPLIVIFFCYGQLVF | Before capping | 25 | 204-228 |
| ESFVIYMFVVHFIIPLIVIFFCYGQLVF | After capping | 28 | 201-228 |
| NESFVIYMFVvhFIIPLIVIFFCYgq | Crystal | 26 | 200-225 |
| TM6: | | | |
| IIMVIAFLICWLPYAGVAFY | Before capping | 20 | 255-274 |
| RMVIIMVIAFLICWLPYAGVAFYIFTH | After capping | 27 | 252-278 |
| ekEVTRMVIIMVIAFLICwLPYAGVAFYIFT | Crystal | 31 | 247-277 |
| TM7: | | | |
| PIFMTIPAFFAKTSAVYNPVI | Before capping | 21 | 285-305 |
| PIFMTIPAFFAKTSAVYNPVI | After capping | 21 | 285-305 |
| IFmTIPAFFAKTSavYNPVIY | Crystal | 21 | 286-306 |

Fig. 4

| | |
|---|---|
| *1200004B 16 | endothelial differentiation sphingolipid G-protein-coupled receptor 1 MGD MGI:1096355 ISS |
| *1300015C04 | purinergic receptor P2Y, G-protein coupled 2   MGD   MGI:105107   ISS |
| *1300018H12 | toll-like receptor 2   MGD   MGI:1346060   ISS |
| *1700025D19 | homolog to putative G protein-coupled receptor   NCBI-nr 7657136 ISS |
| *1810047I05 | L-CCR.   SPTR   O70171   ISS |
| *2900079B22 | 7 transmembrane receptor (rhodopsin family) containing protein Pfam   PF00001 ISS |
| *4833409N04 | prostaglandin F receptor   MGD   MGI:97796   ISS |
| *4921504D23 | homolog to KIAA0001 gene product; putative GPCR; GPCR for UDP-glucose   LocusLink   9934   ISS |
| *4933424L13 | IQ motif containing GTPase activating protein 1 MGD   MGI:1352757   ISS |
| *4933433E02 | similar to OLFACTORY RECEPTOR.  SPTR   Q9QZ18   ISS |
| *1200012O13 | cholecystokinin A receptor   MGD   MGI:99478   ISS |
| *2010001L06 | 7 transmembrane receptor containing protein   Pfam   PF00001 ISS |
| *2210420B03 | endothelial differentiation. G-protein-coupled receptor 6   MGD   MGI:1333809 |
| ISS*3732413I11 | homolog to multiple membrane spanning receptor TRC8 (Patched Related Protein TRC8). SPTR 075485 ISS |
| *4632401H02 | chemokine (C-C) receptor 10   MGD   MGI:1341902   ISS |
| *4930401I05 | MAS1 oncogene MGD   MGI:96918   ISS |
| *4930500J03 | related to NMDA1 Protein (N-methyl-D-aspartate receptor associated protein).  SPTR   Q9V6H7   ISS |
| *4932441H21 | similar to Olfactory Receptor.  SPTR   Q9QZ18   ISS |
| *4933403I07 | follicle stimulating hormone receptor   MGD   MGI:95583   ISS |
| *5430432J15 | purinergic receptor P2Y, G-protein coupled 2   MGD   MGI:105107   ISS |
| *6330420K13 | homolog to Chemokine Receptor-like 2 (G-Protein Coupled Receptor GPR41).   SPTR   O08878   ISS |

Fig. 5

| 1110028I06 | homolog to orphan G-protein coupled receptor    GenPept 8118032 ISS |
| --- | --- |
| 2210416I02 | homolog to P2Y Purinoceptor 5 (P2Y5) (Purinergic Receptor 5) (RB intron-encoded G-Protein Coupled Receptor).    SPTR    P43657    ISS2610302I02 homolog to P2Y Purinoceptor 5 (P2Y5) (Purinergic Receptor 5) (RB Intron-encoded G-Protein Coupled Receptor).    SPTR    P43657    ISS |
| 5730403K14 | G-protein coupled receptor 10    MGD    MGI:99570    ISS |
| 4933415E13 | homolog to G protein-coupled receptor 39    LocusLink    2863    ISS |
| A330106J01 | homolog to rat G protein-coupled receptor LGR4 NCBI-nr 3885470 ISS |
| 2300001H05 | 7 transmembrane receptor (rhodopsin family) containing protein Pfam    PF00001 |
| ISSC530008O16 | 7 TMeceptor (rhodopsin family) containing protein Pfam    PF00001 ISS (98 long in my translation) |
| 3200002M13 | homolog to Orphan G-Protein Coupled Receptor.    SPTR    AAF72870    ISS |

Figure 6 The sequences (43 Blast entries shown) used to generate the multiple sequence alignment with bovine rhodopsin.

```
sp|P28682|OPSB_CHICK Blue-sensitive opsin (Blue cone photorecept...   357   2e-98
sp|P51472|OPSB_ASTFA BLUE-SENSITIVE OPSIN (BLUE CONE PHOTORECEPT...   347   2e-95
sp|P32310|OPSB_CARAU Blue-sensitive opsin (Blue cone photorecept...   337   2e-92
sp|P87365|OPSB_ORYLA BLUE-SENSITIVE OPSIN (BLUE CONE PHOTORECEPT...   330   2e-90
sp|Q9W6A8|OPSB_BRARE Blue-sensitive opsin (Blue cone photorecept...   324   2e-88
sp|P51473|OPSV_XENLA Violet-sensitive opsin (Violet cone photore...   307   2e-83
sp|P51475|OPSP_CHICK Pinopsin (Pineal opsin) (P-opsin) (Pineal g...   302   6e-82
sp|P28684|OPSV_CHICK Violet-sensitive opsin (Violet cone photore...   300   2e-81
sp|P51476|OPSP_COLLI PINEAL OPSIN (P-OPSIN) (PINEAL GLAND-SPECIF...   295   1e-79
sp|O13092|OPSB_SAIBB Blue-sensitive opsin (Blue cone photorecept...   290   3e-78
sp|P51491|OPSB_MOUSE Blue-sensitive opsin (Blue cone photorecept...   290   4e-78
sp|Q90309|OPSU_CARAU ULTRAVIOLET-SENSITIVE OPSIN (ULTRAVIOLET CO...   287   2e-77
sp|P03999|OPSB_HUMAN Blue-sensitive opsin (Blue cone photorecept...   285   1e-76
sp|Q9W6A9|OPSU_BRARE Ultraviolet-sensitive opsin (Ultraviolet co...   283   3e-76
sp|Q63652|OPSB_RAT Blue-sensitive opsin (Blue cone photoreceptor...   283   5e-76
sp|P51490|OPSB_BOVIN Blue-sensitive opsin (Blue cone photorecept...   277   3e-74
sp|P87368|OPSV_ORYLA PUTATIVE VIOLET-SENSITIVE OPSIN (VIOLET CON...   276   4e-74
sp|O42490|OPSP_PETMA PINEAL OPSIN (P-OPSIN) (PINEAL GLAND-SPECIF...   273   3e-73
sp|P04001|OPSG_HUMAN Green-sensitive opsin (Green cone photorece...   269   5e-72
sp|Q95170|OPSR_CAPHI Red-sensitive opsin (Red cone photoreceptor...   268   2e-71
sp|O18913|OPSR_FELCA Red-sensitive opsin (Red cone photoreceptor...   267   3e-71
sp|P35358|OPSG_GECGE Green-sensitive opsin P521 (Green photorece...   266   4e-71
sp|P87367|OPSR_ORYLA RED-SENSITIVE OPSIN (RED CONE PHOTORECEPTOR...   266   6e-71
sp|O18910|OPSG_RABIT Green-sensitive opsin (Green cone photorece...   265   8e-71
sp|P04000|OPSR_HUMAN Red-sensitive opsin (Red cone photoreceptor...   265   1e-70
sp|O35476|OPSG_RAT Green-sensitive opsin (Green cone photorecept...   264   2e-70
sp|P34989|OPSL_CALJA Opsin, longwave 563 nm                          263   3e-70
sp|Q9W6A7|OPSR_BRARE Red-sensitive opsin (Red cone photoreceptor...   263   4e-70
sp|O35478|OPSG_SCICA Green-sensitive opsin (Green cone photorece...   262   8e-70
sp|Q9R024|OPSG_CAVPO Green-sensitive opsin (Green cone photorece...   262   8e-70
sp|O35599|OPSG_MOUSE Green-sensitive opsin (Green cone photorece...   261   1e-69
sp|P32313|OPSR_CARAU Red-sensitive opsin (Red cone photoreceptor...   259   7e-69
sp|P22332|OPSR_ASTFA RED-SENSITIVE OPSIN (RED CONE PHOTORECEPTOR...   258   9e-69
sp|P41592|OPSR_ANOCA Red-sensitive opsin (Red cone photoreceptor...   258   2e-68
sp|O12948|OPSR_XENLA RED-SENSITIVE OPSIN (RED CONE PHOTORECEPTOR...   257   2e-68
sp|P22329|OPSR_CHICK Red-sensitive opsin (Red cone photoreceptor...   253   3e-67
sp|P22330|OPSG_ASTFA Green-sensitive opsin 1 (Green cone photore...   246   6e-65
sp|P22331|OPSH_ASTFA Green-sensitive opsin 2 (Green cone photore...   244   1e-64
sp|O42266|OPSP_ICTPU PARAPINOPSIN                                    229   6e-60
sp|O18912|OPSR_HORSE Red-sensitive opsin (Red cone photoreceptor...   222   7e-58
sp|O18911|OPSG_ODOVI Green-sensitive opsin (Green cone photorece...   222   7e-58
sp|O18914|OPSR_CANFA Red-sensitive opsin (Red cone photoreceptor...   218   1e-56
sp|O13018|OPSO_SALSA Vertebrate ancient opsin                        218   2e-56
```

SYSTEM AND METHODS FOR PREDICTING TRANSMEMBRANE DOMAINS IN MEMBRANE PROTEINS AND MINING THE GENOME FOR RECOGNIZING G-PROTEIN COUPLED RECEPTORS

REFERENCE TO RELATED APPLICATIONS

This application is a continuation of U.S. Ser. No. 10/901,576, filed on Jul. 29, 2004, now abandoned, which claims the benefit of the filing date under 35 U.S.C. § 119(e) of U.S. Provisional Application No. 60/491,334, filed on Jul. 29, 2003, the entire content of which is incorporated herein by reference.

GOVERNMENT SUPPORT

The invention described herein was supported, in whole or in part, by Grant Nos. NIHBRGRO1-GM625523, NIH-R29AI40567, NIH-HD36385, and other grants from other U.S. Government Agencies including the Army Research Office (ARO), the Office of Naval Research (ONR), the Department of Energy (DOE), and the National Science Foundation (NSF). The U.S. Government has certain rights in this invention.

BACKGROUND OF THE INVENTION

Proteins are linear polymers made up of 20 different naturally-occurring amino acids. The particular linear sequence of amino acid residues in a protein is said to define the protein's primary structure. In its natural environment, a protein folds into a three-dimensional structure determined by its primary structure, and by the chemical and electronic interactions is between the protein's individual amino acid constituents and the surrounding aqueous environment, which can include other biomolecules and cellular structures in addition to water.

Studies of known three-dimensional structures have led to the identification of a number of characteristic patterns that appear to be particularly stable and therefore recur within folded proteins. Formed as a result of chemical interactions between different amino acids in the protein, these patterns, which include alpha helices, beta sheets and turns, among others, are referred to as the protein's secondary structure.

The combination of α-helices, β-sheets, turns, and other structures that make up the protein's secondary structure, and the interactions between those structures, determine the protein's tertiary (or three-dimensional) structure. Because a protein's biological properties depend directly on its tertiary structure (i.e., its three-dimensional conformation), understanding that structure is crucial to understanding a protein's biological role and to applying that understanding in such areas as the treatment of disease and the design and development of new pharmaceuticals.

A protein's primary structure can be easily determined using known methods—for example, by identifying the amino acids coded for by a protein's known genetic (nucleotide) sequence. Similarly, known techniques make it relatively easy to identify a protein's secondary structure once the primary structure is determined.

Determining a protein's tertiary structure is more difficult. For some proteins, it is possible to determine tertiary structure through such techniques as x-ray crystallography, or spectroscopic methods such as fluorescence and nuclear magnetic resonance (NMR) studies. However, these techniques can be time-consuming and expensive, and not all proteins are equally amenable to structural examination by these methods.

One such class of proteins is the class of transmembrane/integral membrane proteins. Integral membrane proteins comprise 20-30% of genes (Wallin and von Heijne, 1998) in humans and other forms of life, playing an important role in processes as diverse as ion translocation, electron transfer, and transduction of extracellular signals. One of the most important classes of transmembrane (TM) proteins is the G-protein-coupled receptor (GPCR) superfamily which, upon activation by extracellular signals, initiates an intracellular chemical signal cascade to transduce, propagate, and amplify these signals. GPCRs are involved in cell communication processes and in mediating such senses as vision, smell, taste, and pain. The extracellular signals inciting this transduction are usually chemical, but for the opsin family, it is visible light (electromagnetic radiation). Malfunctions in GPCRs play a role in such diseases as ulcers, allergies, migraine, anxiety, psychosis, nocturnal heartburn, hypertension, asthma, prostatic hypertrophy, congestive heart failure, Parkinson's, schizophrenia, and glaucoma (Wilson and Bergsma, 2000). Indeed, although they comprise 3-4% (Schöneberg et al., 2002) of the human genome, the GPCR superfamily is one of the most important families of drug targets.

GPCRs share a predicted seven-transmembrane helix structure and the ability to activate a G-protein in response to ligand binding. Their natural ligands range from peptide and non-peptide neurotransmitters, hormones, and growth factors to odorants and light. The members of the GPCR superfamily which act through heterotrimeric G-proteins have been classified into six clans (see below). Within a class of GPCRs (for example, adrenergic receptors) there are often several subtypes (for example, nine for adrenergic receptors) all responding to the same endogenous ligand (epinephrine and norepinephrine for adrenergic receptors), but having very different functions in various cells. In addition, many different types of GPCRs are similar enough that they are affected by the antagonists or agonists for other types (e.g., among adrenergic, dopamine, serotonin, and histamine receptors), leading often to undesirable side effects. This makes it difficult to develop drugs to a particular subtype without side effects resulting from cross-reactivity to other subtypes. To design such subtype-specific drugs it is essential to use structure-based methods.

Extensive protein sequence analyses on certain GPCRs has revealed a common topology consisting of a membrane-spanning seven-helix bundle, which is believed to accommodate the binding site for low molecular weight ligands. However, although much effort has been put into elucidating the structure of GPCRs, only a very small number of complete 3D structures of transmembrane proteins are known from experiments (e.g., bacteriorhodopsin and bovine rhodopsin). In fact, there is no atomic-level structure available for any human GPCRs. Consequently, design of subtype-specific drugs for GPCR targets is a very tedious empirical process, often leading to drugs with undesirable side effects.

The difficulty in obtaining three-dimensional structures for GPCRs is obtaining high-quality crystals of these membrane-bound proteins sufficient to obtain high-resolution x-ray diffraction data, and the difficulty of using NMR to determine structure on such membrane-bound systems. For globular proteins, there have been significant advances in predicting the three-dimensional structures by using sequence homologies to families of known structures (Marti-Renom et al., 2000); however, this is not practical for GPCRs, inasmuch as a high-resolution crystal structure is available for only one GPCR, bovine rhodopsin—which has low homology (<35%) to most GPCRs of pharmacological interest. Thus, there is a need for modeling techniques that predict structure and functional characteristics of the members of this class of proteins at a molecular level, especially as a first step, for modeling techniques that predict structural elements such as transmembrane regions.

SUMMARY OF THE INVENTION

The present invention relates to computational methods for predicting the presence of transmembrane regions in proteins, and to computer-implemented apparatus for performing such computations. Related methods are disclosed in co-pending U.S. application Serial No. 09/816,755, and U.S. Provisional Application No. 60/494,971, filed on Aug. 13, 2003, which are both incorporated herein by reference in their entirety.

The invention provides a protocol using a hydrophobic profile based on protein sequence information and/or protein multisequence alignment information to predict transmembrane helical regions in proteins, such as multipass membrane proteins including G-Protein Coupled Receptors (GPCRs). The protocol features a coarse grain sampling methods, such as hydrophobicity analysis, to provide a fast and accurate procedure for predicting TM regions.

In general, in one aspect, the invention features methods and apparatus, including computer program apparatus, implementing techniques for predicting the transmembrane regions in a multipass membrane protein having a plurality of α-helical regions. The techniques can include providing amino acid sequence information and/or sequence alignment information for the multipass membrane protein; plotting a hydrophobic profile using said amino acid sequence information and/or sequence alignment information; assigning/identifying initial TM regions based on the hydrophobic profile; and optionally, capping each identified initial TM regions yield capped TM regions.

In general, in another aspect, the invention features computational models of the structure of transmembrane proteins having a plurality of α-helical regions. The computational models can include computer readable data storage media storing data describing predicted transmembrane regions for potential transmembrane proteins.

In general, in another aspect, the invention features a method to screen a sequence database for transmembrane proteins, such as G Protein-Coupled Receptors (GPCR). The methods of the invention can be used to predict the transmembrane regions based on only primary amino acid sequence information (with or without multi-sequence alignment with similar proteins). Proteins with characteristic organizations of transmembrane regions, such as having seven transmembrane regions, are designated as putative GPCRs.

Thus, one aspect of the invention provides a method for predicting the transmembrane (TM) region(s) of a TM protein, comprising: (1) obtaining amino acid sequence information and/or sequence alignment information for said TM protein; (2) plotting a hydrophobic profile using said amino acid sequence information and/or sequence alignment information; and (3) assigning/identifying initial TM regions based on the global average hydrophobicity of said alignment, or a base_mod within 0.05 thereof; thereby predicting TM region(s) for said TM protein.

In one embodiment, the method further comprising: (4) capping each initial TM regions identified in (3) to yield capped TM regions, based on the presence of helix breakers.

In one embodiment, the TM protein is a multipass TM protein.

In one embodiment, the multipass TM protein is an ion channel, a transporter, or a pump.

In one embodiment, the multipass TM protein has two or more TM regions.

In one embodiment, the multipass TM protein is a seven-TM protein, such as a G Protein-Coupled Receptor (GPCR). The GPCR may be an orphan GPCR or any other GPCR like olfactory receptor (OR). In some embodiments, the GPCR is a rhodopsin-like receptor selected from: olfactory receptor, adenosine receptor, melanocortin receptor, biogenic amine receptor, vertebrate opsin, neuropeptide receptor, prostaglandin receptor, prostacyclin receptor, thromboxane receptor, lipid and peptide receptor, invertebrate opsin, chemokine receptor, chemotactic receptor, somatostatin receptor, opioid receptor, or melatonin receptor; a calcitonin or related receptor selected from: calcitonin receptor, calcitonin-like receptor, CRF receptor, PTH/PTHrP receptor, glucagon receptor, secretin receptor, or latrotoxin receptor; a metabotropic glutamate or related receptor selected from: metabotropic glutamate receptor, calcium receptor, GABA-B receptor, or putative pheromone receptor; a STE2 pheromone receptor; a STE3 pheromone receptor; vermonasal organ (VNO) receptor, or a cAMP receptor.

In one embodiment, the TM region comprises one or more potential α-helical region(s). For example, each of the α-helical region(s) comprises at least about 21 amino acid residues.

In one embodiment, the TM region are all α-helical region(s). In other related embodiments, the TM region has at least one β-sheet, a TM region comprising a β-sheet barrel.

In one embodiment, the hydrophobic profile is based on at least a portion of said TM protein.

In one embodiment, the portion substantially excludes one or more of: the N- or C-terminal region(s) not in contact with lipid bilayers, or inter-TM region loops.

In one embodiment, the hydrophobic profile is based on peak signal analysis.

In one embodiment, the generation of said hydrophobic profile uses the Eisenberg hydrophobicity scale.

In one embodiment, the hydrophobic profile is generated by the SeqHyd profile algorithm.

In one embodiment, the method comprising: (1) obtaining amino acid sequence information and sequence alignment information for said TM protein by: (a) using the sequence of said protein as query, retrieving from a database an ensemble of hit sequences with 20-90% sequence identity, and/or BLAST bit score >200 and E-value >$e^{-100}$; (b) obtaining a multiple sequence alignment of said hit sequences and the sequence of said protein; and, (c) calculating consensus hydrophobicity for every residue position in said alignment; (2) plotting said hydrophobic profile based on said consensus hydrophobicity; (3) assigning/identifying initial TM regions based on the global average hydrophobicity of said alignment, or a local average hydrophobicity, or a base_mod within 0.05 thereof.

In one embodiment, the method further comprises: (4) capping each initial TM regions identified in (3) to yield capped TM regions, based on the presence of helix breakers.

In one embodiment, the database is a protein database, or a polynucleotide database translated in at least one of the six reading frames.

In one embodiment, the ensemble of hit sequences have a uniform distribution of sequences over the entire range of sequence identities.

In one embodiment, the lowest sequence identity to said protein within said ensemble of sequences is about 20-40%.

In one embodiment, the multisequence alignment is performed with ClustalW.

In one embodiment, step (2) is performed with a window size (WS) between 12-20.

In one embodiment, step (3) further comprises identifying additional TM helix region(s) with peak length <23 and peak area <0.8, using local average hydrophobicity more than 0.05 less than said base_mod, if said additional TM helix region(s) are not identified based either on said global average hydrophobicity or said base_mod.

In one embodiment, the helix breakers are Pro (P), Gly (G), Arg (R), His (H), Lys (K), Glu (E), or Asp (D).

In one embodiment, the capped TM regions exclude N- and C-terminal helix breakers.

In one embodiment, the N- and C-termini of said capped TM regions are no more than 6 residues longer or 4 residues shorter than the N- and C-termini of said initial TM regions respectively.

In one embodiment, each residue in each of said capped TM regions has an α-helical conformation.

In one embodiment, the α-helical conformation is characterized by a φ between −37 and −77 degrees, and a ψ between −27 and −67 degrees.

In one embodiment, the α-helical conformation is checked by verifying φ and ψ using PROCHECK.

In one embodiment, the hydrophobic profile is based on the amino acid sequence information alone of said protein.

In one embodiment, the method comprises: (1) obtaining amino acid sequence information for said TM protein; (2) plotting said hydrophobic profile based on the hydrophobicity of each residue within said amino acid sequence; (3) assigning/identifying initial TM regions based on the global average hydrophobicity of said alignment, or a base_mod within 0.05 thereof.

In one embodiment, the method further comprises: (4) capping each initial TM regions identified in (3) to yield capped TM regions, based on the presence of helix breakers.

Another aspect of the invention provides a method of identifying potential transmembrane (TM) proteins, comprising: (1) obtaining amino acid sequence information for one or more candidate TM proteins; (2) for each said candidate TM protein, plotting a hydrophobic profile based on the hydrophobicity of each amino acid residue of said candidate TM protein; and (3) assigning/identifying initial TM regions based on the global average hydrophobicity of said alignment, or a base_mod within 0.05 thereof.

In one embodiment, the amino acid sequence information is obtained from a protein database.

In one embodiment, the amino acid sequence information is obtained from a polynucleotide database translated in at least one of the six reading frames.

In one embodiment, the polynucleotide database is based on a cDNA library or a coding sequence (CDS) library predicted from sequenced genomic DNAs.

In one embodiment, the cDNA library is a mouse, rat, or human cDNA library.

In one embodiment, the protein database has more than 20,000 sequences.

In one embodiment, step (3) further comprises identifying additional TM region(s) with peak length <23 and peak area <0.8, using local average hydrophobicity more than 0.05 less than said base_mod, if said additional TM region(s) are not identified based either on said global average hydrophobicity or said base_mod.

In one embodiment, the method further comprises designating any candidate TM proteins with seven initial TM regions as GPCR, wherein each of said TM regions comprises at least 21 residues.

In one embodiment, the method further comprises verifying identified GPCR by experimental data selected from x-ray crystallography or nuclear magnetic resonance (NMR), or by first principles procedures.

Another aspect of the invention provides a computer executable software code stored in a computer readable medium, which upon execution carries out a method for predicting the transmembrane (TM) region(s) of a TM protein, said method comprising: (1) obtaining amino acid sequence information and/or sequence alignment information for said TM protein; (2) plotting a hydrophobic profile using said amino acid sequence information and/or sequence alignment information; and (3) assigning/identifying initial TM regions based on the global average hydrophobicity of said alignment, or a base_mod within 0.05 thereof; thereby predicting TM region(s) for said TM protein.

Another aspect of the invention provides a system for predicting the transmembrane (TM) region(s) of a TM protein, comprising: (1) data input module for obtaining amino acid sequence information and/or sequence alignment information for said TM protein; (2) a profile generation module for plotting a hydrophobic profile using said amino acid sequence information and/or sequence alignment information; and (3) a TM region identification module for assigning/identifying initial TM regions based on the global average hydrophobicity of said alignment, or a base_mod within 0.05 thereof.

Each module can be implemented either independently or in combination with one or more of the other modules. A module can be implemented in hardware in the form of a DSP, ASP, Reprogrammable ROM device, or any other form of integrated circuit, in software executable on a general or special purpose computing device, or in a combination of hardware and software.

Another aspect of the invention provides a computational model of the TM regions of a transmembrane protein, the computational model comprising: a computer-readable memory storing data describing one or more predicted TM regions for the transmembrane protein, the predicted TM regions being generated according to the subject method, such as TM2ndS.

It is contemplated that all embodiments described above, even embodiments under different aspects of the inventions, are to be freely combined with any one or more other embodiments of the invention whenever appropriate.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 Hydrophobicity profile from TM2ndS for bovine rhodopsin at window size of WS=14. The dashed line (at 0.07) is the base_mod (described in Step 1, average consensus hydrophobicity and initial TM assignment) used as the baseline in identifying hydrophobic regions. The predicted TM domains are indicated by the orange dash dot lines (after capping). The dotted lines show the predictions before helix capping. Each tick mark indicates the sequence number for the alignment based on bovine rhodopsin (100 residues per panel). The residues at every fifth position are indicated below each panel. The partition of helix 7 into two parts results from the hydrophilic residues near its center.

FIG. 2 The transmembrane helical predictions (labeled as after capping) from TM2ndS compared with helix ranges from the bovine rhodopsin x-ray crystal structure. The predictions before TM2ndS capping are also shown. Those residues in the crystal structure that fall outside the range of α-helicity (using analysis described in Step 1c, Helix Capping in TM2ndS) are indicated in lowercase letters. Sequences in this figure is represented by SEQ ID NOs: 1-20.

FIG. 4 Illustrative initial results (true positives) from mouse genome cDNA library search using TM2ndS.

FIG. 5 Some annotated GPCRs not identified by TM2ndS. It should be noted that these sequences are all of sizes less than 250 residues, which is at least partially responsible for the failure of TM2ndS to identify the seven requisite TM helices.

FIG. 6: The sequences (43 Blast entries shown) used to generate the multiple sequence alignment with bovine rhodopsin.

DETAILED DESCRIPTION OF THE INVENTION

I. Overview

Figure 3:
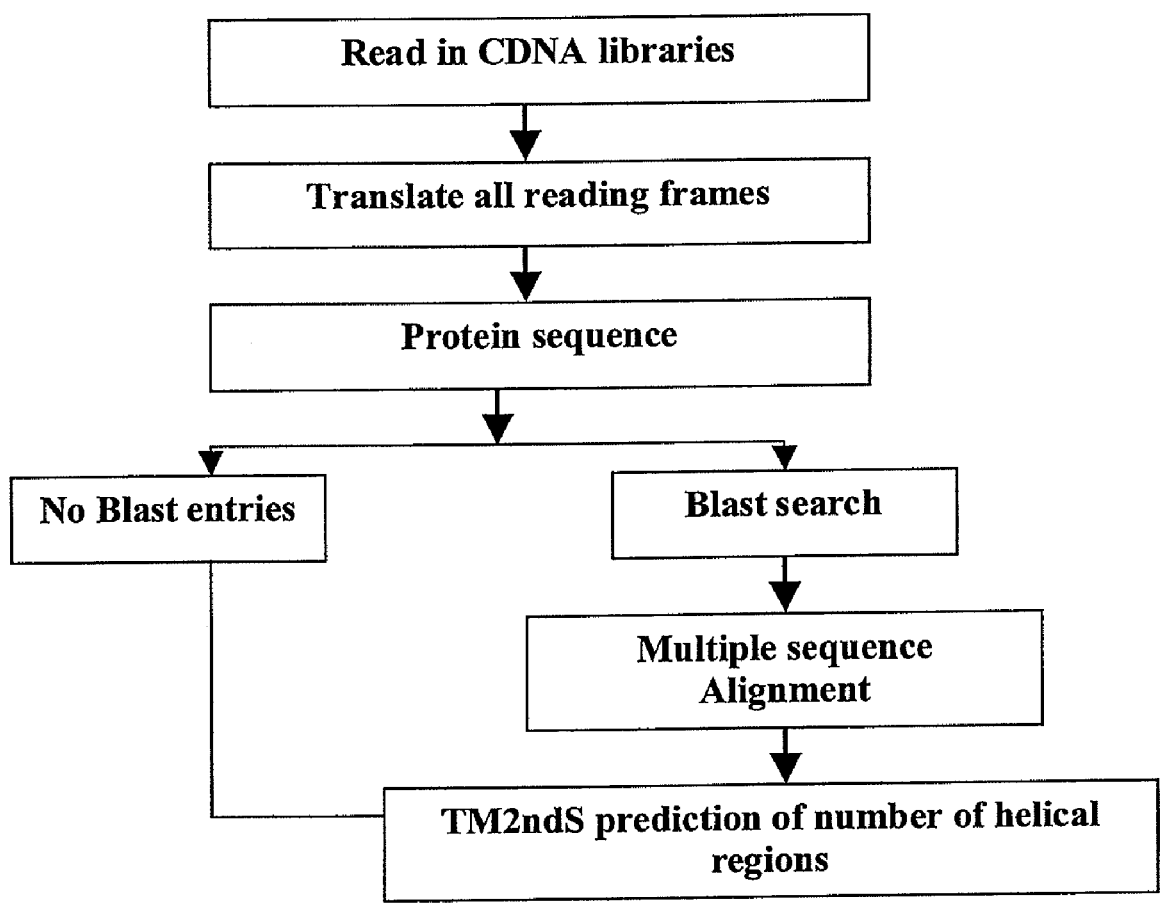
FIG. 3 Schematic drawings showing procedures for genome annotation for membrane proteins using secondary structure prediction by TM2ndS.

The methods, computer programs, and apparatus of the invention provide a system to aid the theoretical methods adequate for ab initio or first principles prediction of transmembrane regions of transmembrane proteins, including single-pass and multipass transmembrane proteins (such as GPCRs). In certain embodiments of the invention, the system of the invention can provide results that aid the structure-based drug design for GPCR targets.

In one preferred embodiment, the system of the invention is the TM2ndS method for first principles prediction of transmembrane regions for transmembrane proteins (e.g., GPCRs) from primary sequence, without using homology modeling.

The methods and systems of the invention are partly based on the organizing principle that a transmembrane protein has a single polypeptide chain with a single or multiple (usually more than 2-3, preferably seven) helical TM domains threading through the membrane. Prediction of the TM helical regions for transmembrane proteins from their primary sequences partly rests on the assumption that the outer regions of the TM helices (in contact with the hydrophobic tails of the lipids) should be hydrophobic, and that this character should be largest near the center of the membrane. Partly based on this concept, the prediction method (e.g., TM2ndS) generates a hydrophobic profile for TM region prediction.

The methods of the invention are validated as described in the Examples below by applying the method to several GPCRs, where the validation has been based on the comparison of the predicted binding site to experimental binding and mutation data, including the only high-resolution crystal structure available for a GPCR, bovine rhodopsin.

Details of the different embodiments of the invention are described below.

The present invention provides a computational method for identifying a Tran membrane protein and/or predicting the TM regions of Tran membrane proteins such as single, or multiphase membrane proteins as exemplified by G-protein coupled receptors (Gapers). In brief, starting with the primary amino acid sequence for a putative Tran membrane protein (obtained, for example, from public or commercial databases such as GENBANK® (genetic sequence database), EMBL, DDBJ, etc.), the method of the invention predicts the transmembrane helical domains for the protein based on its hydrophobicity profile.

The techniques described herein can be implemented using a modeling system. The modeling system of the invention includes a general-purpose programmable digital computer system of special or conventional construction, including a memory and a processor for running a modeling program or programs. The modeling system may also include input/output devices, and, optionally, conventional communications hardware and software by which a computer system can be connected to other computer systems.

In some embodiments, the modeling system of the invention can be implemented on a single computer system. In a related embodiment, the functions of the model system of the invention can be distributed across multiple computer systems, such as on a network. Those skilled in the art will recognize that the system of the invention can be implemented in a variety of ways using known computer hardware and software, such as, for example, a Silicon Graphics Origin 2000 server having multiple R10000 processors running at 195 MHz, each having 4 MB secondary cache, or a dual processor Dell PowerEdge system equipped with Intel PentiumIII 866 MHz processors with 1 Gb of memory and a 133 MHz front side bus. More advanced and/or powerful systems are constantly being produced, and are all commercially available.

In some embodiments, the steps of the subject method can be implemented by a computer system comprising modules, each adapted to perform one or more of the steps. Each module can be implemented either independently or in combination with one or more of the other modules. A module can be implemented in hardware in the form of a DSP, ASP, Reprogrammable ROM device, or any other form of integrated circuit, in software executable on a general or special purpose computing device, or in a combination of hardware and software.

In general, the method starts with an amino acid sequence obtained from memory or some other source, such as a commercial database as discussed above (e.g., those accessible from the internet). The sequence information is used to identify transmembrane regions (see below for detail). In certain embodiments, a multisequence alignment is needed. In these embodiments, homologous sequences of the target protein sequence can be retrieved by a sequence homology search program, such as NCBI's BLASTp (Altschul et al., 1990, 1997, incorporated by reference herein). Certain retrieved sequences meeting certain predetermined criteria can then be aligned by, for example, a multiple sequence alignment program, such as ClustalW (Thompson et al., 1994, incorporated by reference herein). The final output from this step is a multisequence alignment. Each amino acid residues in the multisequence alignment is then converted to a hydrophobicity value based on, for example, the Eisenberg hydrophobicity scale (Eisenberg et al., 1982, incorporated by reference herein). Such data are in turn used to calculate the consensus hydrophobicity for every residue position in the alignment.

In some other embodiments, the amino acid sequence of the target protein is directly converted to its hydrophobicity values based on the Eisenberg hydrophobicity scale.

A hydrophobicity profile may be generated based on the consensus hydrophobicity of the alignment, or the hydrophobicity of the amino acid sequence, as determined by any of the above protocols. Initial TM regions are assigned according to this hydrophobicity profile (see details below). Such initial TM regions can optionally be further refined, by defining helix break points at either or both ends of each initial TM regions.

The techniques and apparatus described herein may have useful application in the prediction of any transmembrane protein having one or more membrane-spanning regions, including α-helices and/or β-sheets, etc., where the protein's primary structure (amino acid sequence) is known, and, better yet, for which an experimental or theoretical helical template is available. In particularly advantageous implementations, the techniques and apparatus are useful in predicting the TM regions in proteins having a relatively large number (e.g., about 4 or more) of membrane-spanning regions (e.g. α-helical regions), such as the seven-helical GPCRs.

The output TM regions can be used in further studies, including, for example, 3-D structure determination using the first principles/ab initio protocols (such as MembStruk 3.5, as disclosed in U.S. Ser. No. 60/494,971, filed on Aug. 13, 2003), and ligand docking studies using the HierDock or other similar protocols. These studies can be directed to modeling receptor binding sites, or to the purpose of identifying natural or synthetic receptor ligands, or to develop synthetic receptors that exhibit behavior analogous to naturally-occurring GPCRs. The predicted structures can also be useful in identifying regions of cellular receptors that bind microbial pathogens. Subsequently using this model of the first step of pathogenesis, one could design competitive inhibitors either on the receptor or for the microbial surface structures.

The instant invention can be implemented in digital electronic circuitry, or in computer hardware, firmware, software, or combinations thereof. Apparatus of the invention can be implemented in one or more computer program products tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

II. Definitions

The terms used in this specification (including the ones listed below) generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. Thus such discussion should not be construed to be limiting. The scope an meaning of any use of a term will be apparent from the specific context in which the term is used.

"About" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

"Protein backbone structure" or grammatical equivalents herein is meant the three-dimensional coordinates that define the three-dimensional structure of a particular protein. The structures which comprise a protein backbone structure (of a naturally occurring protein) are the nitrogen, the carbonyl carbon, the α-carbon, and the carbonyl oxygen, along with the direction of the vector from the α-carbon to the β-carbon.

The protein backbone structure which is input into the computer can either include the coordinates for both the backbone and the amino acid side chains, or just the backbone, i.e., with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogens attached to the nitrogen and α-carbon).

Optionally, the protein backbone structure may be altered prior to the analysis outlined below. In this embodiment, the representation of the starting protein backbone structure is reduced to a description of the spatial arrangement of its secondary structural elements. The relative positions of the secondary structural elements are defined by a set of parameters called supersecondary structure parameters. These parameters are assigned values that can be systematically or randomly varied to alter the arrangement of the secondary structure elements to introduce explicit backbone flexibility. The atomic coordinates of the backbone are then changed to reflect the altered supersecondary structural parameters, and these new coordinates are input into the system for use in the subsequent protein design automation. For details, see U.S. Pat. No. 6,269,312, the entire content incorporated herein by reference.

The methods of the invention may include steps of comparing sequences to each other, including wild-type sequence to one or more mutants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, "-", or "Δ") in the polymer sequence not containing the inserted or deleted residue.

"Homologous", in all its grammatical forms and spelling variations, refers to the relationship between two proteins that possess a common evolutionary origin, including proteins from superfamilies in the same species of organism, as well as homologous proteins from different species of organism.

Such proteins (and their encoding nucleic acids) have sequence homology, as reflected by their sequence similarity, whether in terms of percent identity or by the presence of specific residues or motifs and conserved positions.

The term "sequence similarity", in all its grammatical forms, refers to the degree of identity or correspondence between nucleic acid or amino acid sequences that may or may not share a common evolutionary origin (see, Reeck et al., supra).

"Polypeptide," "peptide" or "protein" are used interchangeably to describe a chain of amino acids that are linked together by chemical bonds called "peptide bonds." A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Raw alignment score" or the score of an alignment, S, is calculated as the sum of substitution and gap scores. Substitution scores are given by a look-up table (see PAM, BLOSUM62 etc.). Gap scores are typically calculated as the sum of G, the gap opening penalty and L, the gap extension penalty. For a gap of length n, the gap cost would be G+Ln. The choice of gap costs, G and L is empirical and may be defined by user, but it is customary to choose a high value for G (e.g. 10-15) and a low value for L (e.g. 1-2). BLAST 2.0 and PSI-BLAST use "affine gap costs" which charge the score −a for the existence of a gap, and the score −b for each residue in the gap. A gap of k residues therefore receives a total score of −(a+bk) and a gap of length l receives the score −(a+b). Gap creation and extension variables a and b are inherent to the scoring system in use.

"Bit score" is a numeric value (positive integer) calculated by the BLAST program based on the goodness of match between the query sequence and the hit sequence. In general, the higher the sequence homology/identity, and the longer the homologous region, the higher the bit score. The value S' is derived from the raw alignment score S in which the statistical properties of the scoring system used have been taken into account. Because bit scores have been normalized with respect to the scoring system, they can be used to compare alignment scores from different searches.

To convert a raw score S into a normalized score S' expressed in bits, one uses the formula S'=(lambda*S−ln K)/(ln 2), where lambda and K are parameters dependent upon the scoring system (substitution matrix and gap costs) employed (Karlin & Altschul (1990) Proc. Natl. Acad. Sci. USA 87:2264-2268; Altschul & Gish (1996) Meth. Enzymol. 266:460-480; Altschul et al. (1997) Nucleic Acids Res. 25:3389-3402; all incorporated herein by reference). For determining S', the more important of these parameters is lambda. The "lambda ratio" quoted here is the ratio of the lambda for the given scoring system to that for one using the same substitution scores, but with infinite gap costs (Altschul & Gish, supra). This ratio indicates what proportion of information in an ungapped alignment must be sacrificed in the hope of improving its score through extension using gaps. It is empirically found that the most effective gap costs tend to be those with lambda ratios in the range 0.8 to 0.9.

"E-value" or "expectation value" represents the number of different alignments with scores equivalent to or better than S that are expected to occur in a database search by chance. The lower (closer to 0) the E value, the more significant the score. An identical hit sequence has the lowest possible E-value, or 0. E-value is generally expressed as $a \times e^{-n}$, where n is an integer.

III. Exemplary Embodiments of the Invention
(A) Predicting Transmembrane Regions for Transmembrane Proteins Methods of the invention (e.g., exemplified by TM2ndS) uses the hydrophobic profile of either multisequence alignment or primary amino acid sequence of single/multipass membrane proteins to assign the TM regions (helical or n-sheet barrel).

In general, the TM prediction methods of the invention comprise the following steps:
1. obtaining amino acid sequence information and/or sequence alignment information for said TM protein;
2. plotting a hydrophobic profile using said amino acid sequence information and/or sequence alignment information;
3. assigning/identifying initial TM regions based on the global average hydrophobicity of said alignment, or a base_mod within 0.05 thereof; and
4. optionally, capping each initial TM regions identified in (3) to yield capped TM regions, based on the presence of helix breakers.

Some of the details of these steps are discussed below. It is emphasized here that these steps provide general guidelines for carrying out the methods of the invention, and minor deviations based on equivalent steps or protocols are within the spirit of the invention. In addition, all or several steps can be automated into a single procedure that can optionally executed by a computer program. Thus, a target sequence can be fed to the program and the result at the end is a final prediction with several (if any) TM regions.

In general, prediction of the TM regions for transmembrane proteins from their primary amino acid sequences partly rests on the assumption that the outer regions of the TM regions (in contact with the hydrophobic tails of the lipids) should be hydrophobic, and that this character should be largest near the center of the membrane. The TM2ndS-like method uses this concept to generate a hydrophobic profile.

Step 1: Obtaining Primary Amino acid Sequence and (Optional) Multi-Sequence Alignment In certain embodiments, the methods of the invention can directly use the primary amino acid sequence (including amino acid sequence translated from a polynucleotide sequence) for conversion to hydrophobicity values.

In other embodiments, the methods of the invention take advantage of a multisequence alignment of the target primary amino acid sequence. Such multisequence alignment result is used to derive consensus hydrophobicity for every residue position in the alignment, which is equivalent to the hydrophobicity values of the original primary amino acid sequence.

In either embodiments, a hydrophobic profile can be established by converting amino acid sequence or sequence alignment information into hydrophobicity values using a hydrophobicity scale. Peak signal analysis can then be performed based on the hydrophobic profile plot.

In certain embodiments, the Prift hydrophobicity scale (Cornette et al., 1987, incorporated herein by reference in its entirety) may be used. But in certain cases, the hydrophobicity index value for Arg in the Prift hydrophobicity scale may be opposite that expected for a charged residue, thus leading to potentially incorrect assignments.

Thus in preferred embodiments of the invention, the Eisenberg hydrophobicity scale (Eisenberg et al., 1982, incorporated herein by reference in its entirety), which is based on sound thermodynamic arguments, may be used. This scale has a range from −1.76 to 0.73 and works well for Arg and other residues to give consistent TM predictions for the many systems so far investigated.

In those embodiments where multi-sequence alignment is necessary, the target sequence is used as a query to retrieve an ensemble of homologous sequences meeting certain pre-determined criteria. To retrieve homologous sequences, sequence search engines/programs such as NCBI's BLASTp search (Altschul et al., 1990, 1997, incorporated herein by reference in its entirety) may be used. Among the retrieved hit sequences, those with sequence identity of about 20-90%, and/or bit scores >200, but not identical (to avoid numerical bias in later calculations) to the target sequence (E-value >$e^{-100}$) are selected. Preferably, to avoid potential bias, an even distribution of sequences among the entire range of sequence homology/identity is selected, if possible.

The BLAST programs, including BLASTp, are described in detail in the NCBI BLAST website. The website also provides a BLAST Program Selection Guide to help a user in selecting the most suitable BLAST programs for specific needs and specific query sequences. The website also links to a number of protein and polynucleotide databases that can be search by the BLAST programs. The entire contents of the NCBI Blast website are incorporated herein by reference.

In performing a BLAST search, default parameters provided by the program can generally be used. However, in certain situations, user may opt to change certain alternative parameters (e.g., by selecting among many pull-down menus or providing numeric values in parameter fields) as offered by the program to suit specific needs.

In selecting hit sequences for subsequent multi-sequence alignment, the method prefers an ensemble of sequences providing a uniform distribution of sequence identities from 20% to 100%, preferably 20-90%, or 35 to 90%. In other words, selecting clusters of, or disproportional numbers of homologous sequences with very similar values in sequence identity (e.g., all about 50-55% identical) are disfavored if possible. For a typical target sequence, about 20-100 sequences, preferably about 30-80, or 40-50 sequences are selected. In the case of bovine rhodopsin, 43 homologous sequences may be selected (see FIG. 6).

These homologous sequences, plus the target sequence are then used in a program such as ClustalW (Thompson et al., 1994, the entire contents of which incorporated herein by reference) to generate a multiple sequence alignment. This sequence alignment preferably includes sequences with identities to the target sequence as low as about 20%, 35%, 40%, 45%, or about 50%. In general, the method may include sequences with higher or lower non-zero E-values, but including too low a homology (higher E-values) might lead to additional alignment problems.

In an exemplary embodiment, such a step can be performed using the SeqHyd hydrophobic profile algorithm, which is based on peak signal analysis of the hydrophobic profile. SeqHyd requires a multiple sequence alignment using sequences related to the target sequence (e.g. bovine rhodopsin).

Step 2: Hydrophobicity for Each Amino Acid Residue or Average Consensus Hydrophobicity In one embodiment of the invention, where no multisequence alignment is performed, the amino acid sequence can be directly converted, according to the chosen hydrophobicity scale, to hydrophobicity values at each residue positions.

In other embodiments where a multisequence alignment is performed, the equivalent step is to calculate the consensus hydrophobicity for every residue position in the alignment. This consensus hydrophobicity is the average hydrophobicity (e.g., using the Eisenberg hydrophobicity scale) of all the amino acids in that position over all the sequences in the multiple sequence alignment, optionally weighted for the frequency of occurrence of each particular amino acid at that position.

To plot a hydrophobic profile of the sequence or the aligned sequences, the method calculates the average hydrophobicity over a chosen window size (WS) of residues around every residue position, using WS ranging from 12 to 20.

For each residue, the window of calculation is preferably symmetric (with equal number of residues to the N- and C-terminal sides of the residue in question), although it is not impossible under certain circumstances to use asymmetric windows, which extend to different numbers of residues to the N- and C-terminal sides of the residue in question.

This average value of hydrophobicity at each sequence position is plotted to yield the hydrophobic profile (see, for example, FIG. 1 for WS=14 in the rhodopsin example). The baseline for this profile serves as the threshold value for determining the TM regions and is calculated as follows in step 3.

Step 3: Assigning/Identifying Initial TM Regions

First, the method obtains the global average hydrophobicity value over all residues in the protein. In some embodiments, the method may include a step that excludes the solvent-exposed regions of the sequences, such as the amino terminus region (e.g., 34 residues in rhodopsin) and/or the carboxyl terminus region (e.g., 42 residues in rhodopsin) that are outside the TM regions. In certain embodiments, the solvent-exposed regions may also include some inter-TM region loops, especially those large loops with more than about 20 amino acids. These regions are accessible to solvent (e.g. water) on the intracellular or extracellular region, and tend to have non-insignificant numbers of hydrophilic residues that would skew the global average value.

This global average established a baseline that can be used for determining initial TM regions (peaks on the hydrophobic profile plot). If this baseline thus obtained does not resolve the expected number of peaks, then the method automatically changes the baselines over a range of a pre-determined value, e.g., 0.05, from the global average. The baseline closest to the average that yields the expected number of (seven for GPCR) peaks ("base_mod") is used for TM region prediction. The base_mod provides the basis for the accurate determination of the TM regions in the sequence. This final baseline may be interpreted physically as a $\Delta G=0$ value above which residues are thermodynamically stable in the transmembrane and below which they are not. This baseline is unique to the particular protein to which it is being applied, with its individual environmental factors (water clusters, ions, hydrophobic or hydrophilic ligand or interhelical interactions, membrane composition) that may change the relative stability of any particular residue.

Below WS=12, the fluctuations in hydrophobicity (noise) tend to be too large to be useful. The lowest WS that yields seven peaks (with peak length >10 and <50, and peak area >0.8) is denoted as $WS_{min}$. The peaks ranges for $WS_{min}$ are used as input for the helix-capping module discussed in the next section.

In certain embodiments, assigning the TM region to certain short helices may be a problem, because they have shorter lengths and lower intensity peak hydrophobicity compared with all the other helices. This has been observed for some GPCRs (Vaidehi et al., 2002), especially helix 7 of the bovine rhodopsin. In that case, the low intensity of helix 7 arises because it has fewer highly hydrophobic residues (Ile, Phe, Val, and Leu) and because it has a consecutive stretch of hydrophilic residues (e.g., KTSAVYN, SEQ ID NO: 21).

These short stretches of hydrophilic residues (including Lys-296) are involved in the recognition of the aldehyde group of 11-cis-retinal in rhodopsin. For such cases, the method uses the local average of the hydrophobicity (defined as a line from minimum to minimum around this peak, or the average hydrophobicity of all residues excluding those solvent-exposed N-terminal, C-terminal, and/or loop residues) as the baseline for assigning the TM predictions.

In a preferred embodiment, the method automatically applies this additional criteria when the peak length is <23, the peak area is <0.8, and the local average is >0.05 less than the base_mod. In other words, this local average is automatically applied for proteins where the residues are relatively hydrophilic but in which the helix might still be stable because of local environmental factors (mentioned above) that stabilize these residues.

Step 4: (Optional) Helix Capping

It is possible that the actual length of the helix would extend past the membrane surface. Thus, the method provides an optional step to fine-tune the N- and C-terminal ends of the predicted TM helical regions. This helix-capping step is aimed at capping each helix at the top and bottom of the TM domain, and is premised on properties of known helix breaker residues. In addition, the method restricts the procedure so as not to extend the predicted TM helical region more than six residues.

In certain preferred embodiments, potential helix breakers include P and G; positively charged residues R, H, and K; and negatively charged residues as E and D.

In this step, the method first searches up to four residues from the edge going inwards from the initial TM prediction obtained from the previous section for a helix breaker. If it finds one, then the TM helix edges are kept at the initial values. In an alternative embodiment, the TM helix edges are broken off at the helix breaker, either including or excluding the helix breaker.

However, if no helix breaker is found, then the TM helical region is extended until a breaker is found, but with the restriction that the helix not be extended more than six residues on either side. Again, the TM helix edges are broken off at the helix breaker, either including or excluding the helix breaker.

In certain embodiments, regardless of capping step, the final shortest helical assignment allowed is 21, corresponding to the shortest known helical TM region. This lower size limit prevents incorporation of narrow noise peaks into TM helical predictions.

This algorithm has been successful used for predicting the structure for about 10 diverse GPCR classes (Vaidehi et al., 2002). In each case, the predicted binding site and binding energy agrees well with available experimental data, providing some validation of the TM helical region prediction. However, only for bovine rhodopsin have precise comparisons to an experimental structure been made (see below). For example, FIG. 2 compares the predictions of TM helical regions for bovine rhodopsin to the TM helical regions as assigned in the crystal structure (Palczewski et al., 2000).

In certain embodiments, the defined TM helical regions can be further checked to determine which residues have an α-helical conformation. For this, the method analyses the Φ-Ψ angles using, for example, PROCHECK (Laskowski et al., 1993, incorporated herein by reference), and considers the experimental structure to be in an α-helix if $-37<\Phi<-77$ and $-27<\psi<-67$. This may lead to slightly shorter helices than quoted in the crystal structure (see the lowercase letters in FIG. 2, which indicate residues which are outside the above range but quoted as helices in the experimental article).

A specific embodiment of the subject transmembrane region-predicting method is in the form of the TM2ndS program, which is used to predict TM regions in Trabanino et al., Biophysical Journal 86: 1904-1921, 2004, the entire content of which is incorporated herein by reference.

(B) Transmembrane Proteins

The methods and apparatus of the invention are generally applicable to the prediction of TM regions (α-helix or β-sheet barrel) of any membrane proteins, especially those proteins comprised predominantly of transmembrane structures, e.g., multi-pass transmembrane protein (such as various pumps, ion channels and transporters). The methods and apparatus are especially well-suited for those 7-TransMembrane (7-TM) proteins, such as GPCRs.

In certain embodiments, the transmembrane domains are mostly or all alpha-helices.

In one embodiment, the methods of the invention are used to predict the secondary and tertiary structure of the transmembrane region of a transmembrane protein.

Thus, the methods of the invention can be used for TM helical region prediction for: G protein-coupled receptors, receptor tyrosine kinases, cytokine receptors, and ion channels. In certain embodiments the method described herein is used for predicting the structure of, and/or identifying ligands for "orphan receptors" for which no ligand is known.

In some embodiments, the receptor is a cell surface receptor, such as: a receptor tyrosine kinase, for example, an EPH receptor; an ion channel; a cytokine receptor; an multisubunit immune recognition receptor; a chemokine receptor; a growth factor receptor; or a G-protein coupled receptor, such as a chemoattractant peptide receptor; a neuropeptide receptor; a light receptor; a neurotransmitter receptor; or a polypeptide hormone receptor.

In a preferred embodiment, the receptor comprises 2 or more, preferably 3 or more, 4 or more transmembrane domains. In a preferred embodiment, the receptor comprises 7 transmembrane domains.

G Protein-Coupled Receptors

GPCRs share a predicted seven-transmembrane helix structure and the ability to activate a G-protein ($G_i$, $G_a$, $G_o$, etc.) in response to ligand binding. Their natural ligands range from peptide and non-peptide neurotransmitters, hormones, and growth factors to odorants and light. The members of the GPCR superfamily which act through heterotrimeric G-proteins have been classified into six clans, as set out below:

Classification of G-Protein Coupled Receptors

1. Clan A: rhodopsin like receptors

Family I: Olfactory receptors, adenosine receptors, melanocortin receptors and others.

Family II: Biogenic amine receptors.

Family III: Vertebrate opsins and neuropeptide receptors.

Family IV: Invertebrate opsins.

Family V: Chemokine, chemotactic, somatostatin, opioids and others.

Family VI: Melatonin receptors and others.

2. Clan B: calcitonin and related receptors

Family I: Calcitonin, calcitonin-like, and CRF receptors.

Family II: PTH/PTHrP receptors.

Family III: Glucagon, secretin receptors and others.

Family IV: Latrotoxin receptors and others.

3. Clan C: metabotropic glutamate and related receptors

Family I: Metabotropic glutamate receptors

Family II: Calcium receptors

Family III: GABA-B receptors

Family IV: Putative pheromone receptors

4. Clan D: STE2 pheromone receptors

5. Clan E: STE3 pheromone receptors
6. Clan F: cAMP receptors

For example, one group of members of Clan A, Family I are the olfactory (odor) receptors (ORs) in the mammalian olfaction system. These receptors, unlike many other GPCRs that are designed for the specific recognition of few ligands, exhibit a combinatorial response to thousands of odorant molecules. See Malnic, B., et al. (1999) Cell 96, 713-723. A single odor elicits response from multiple receptors and a single receptor also responds to multiple odorants, so every odorant has been thought to have a unique combination of responses from several receptors. Odor detection is mediated by approximately 1,000 ORs that are G protein coupled membrane-bound proteins. Malnic et al. recently reported the differential responses of individual mouse OR neurons to 24 organic odor compounds (linear alcohols, acids, diacids, and bromoacids with four to nine carbons) by using $Ca^{2+}$-imaging techniques, followed by single-cell reverse transcription-PCR to determine the sequence of the responsive OR. These results lead to the compelling question of "what is the molecular basis of odor recognition?" Such questions can be answered only with an understanding of the atomic-level structure of these ORs.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery. In addition, STRs have been identified for which the natural ligands are unknown; these receptors are termed "orphan" G protein-coupled receptors, as described above. Examples include receptors cloned by Neote et al. (1993) Cell 72, 415; Kouba et al. FEBS Lett. (1993) 321, 173; Birkenbach et al. (1993) J. Virol. 67, 2209.

The "exogenous receptors" may be any G protein-coupled receptor which is exogenous to a cell of interest. This receptor may be a plant or animal cell receptor. Studying plant cell receptors may be useful in the development of, for example, herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline, histamine, noradrenaline, noradrenaline, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheremones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activiating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Such ligands or derivatives thereof may be used in the HierDock protocol for prediction of ligand binding and mutagenesis study in silico. Such ligands may also be used as a library when screening for potential ligands for orphan GPCRs.

Suitable examples of G-protein coupled receptors include, but are not limited to, dopaminergic, muscarinic cholinergic, α-adrenergic, β-adrenergic, opioid (including delta and mu), cannabinoid, serotoninergic, and GABAergic receptors. Preferred receptors include the 5HT family of receptors, dopamine receptors, C5a receptor and FPRL-1 receptor, cyclo-histidyl-proline-diketoplperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Y1 or galanin. Other suitable receptors are listed in the art.

Specifically, preferred G protein-coupled receptors include α1A-adrenergic receptor, α1B-adrenergic receptor, α2-adrenergic receptor, α2B-adrenergic receptor, 1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. The term 'receptor,' as used herein, encompasses both naturally occurring and mutant receptors.

The homology of STRs is discussed in Dohhnan et al., Ann. Rev. Biochem., (1991) 60:653-88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

Cytokine Receptors

In one embodiment, the target transmembrane protein is a cytokine receptor.

Cytokines are a family of soluble mediators of cell-to-cell communication that includes interleukins, interferons, and colony-stimulating factors. The characteristic features of cytokines lie in their functional redundancy and pleiotropy.

Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the Jak protein tyrosine kinase family, with resultant phosphorylation of the STAT transcriptional activator factors. IL-2, IL-7, IL-2 and Interferon γ have all been shown to activate Jak kinases (Frank et al (1995) *Proc Natl Acad Sci USA* 92:7779-7783); Scharfe et al. (1995) *Blood* 86:2077-2085); (Bacon et al. (1995) *Proc Natl Acad Sci USA* 92:7307-7311); and (Sakatsume et al (1995) *J. Biol Chem* 270:17528-17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al. (1995) *Proc Natl Acad Sci* 92:5482-5486) and (Musso et al (1995) J Exp Med. 181:1425-1431). The Jak kinases have also been shown to be activated by numerous ligands that signal via cytokine receptors such as, growth hormone and erythropoietin and IL-6 (Kishimoto (1994) Stem cells Suppl 12:37-44).

There are major families of cytokine receptors. Some are members of the Ig supergene family (e.g. IL-1 receptor), others are members of the nerve growth factor receptor family (e.g., TNF), but the majority are members of the haematopoietic growth factor family (e.g., IL-3, GM-CSF). Yet other cytokine receptors do not belong to a family, e.g., IFN-gamma. See Foxwell et al., Clin Exp Immunol. 1992 November; 90(2):161-9.

Multisubunit Immune Recognition Receptor (MIRR)

In another embodiment, the methods of the invention can be used to predict the 3-D structure of a multisubunit receptor with multiple transmembrane domains. Receptors can be comprised of multiple proteins referred to as subunits, one category of which is referred to as a multisubunit receptor is a multisubunit immune recognition receptor (MIRR). MIRRs include receptors having multiple noncovalently associated subunits and are capable of interacting with src-family tyrosine kinases. MIRRs can include, but are not limited to, B cell antigen receptors, T cell antigen receptors, Fc receptors and CD22. One example of an MIRR is an antigen receptor on the surface of a B cell. To further illustrate, the MIRR on the surface of a B cell comprises membrane-bound immunoglobulin (mIg) associated with the subunits Ig-α and Ig- or Ig-γ, which forms a complex capable of regulating B cell function when bound by antigen. An antigen receptor can be functionally linked to an amplifier molecule in a manner such that the amplifier molecule is capable of regulating gene transcription.

Signal transduction pathways for MIRR complexes are capable of regulating the biological functions of a cell. Such functions can include, but are not limited to the ability of a cell to grow, to differentiate and to secrete cellular products. MIRR-induced signal transduction pathways can regulate the biological functions of specific types of cells involved in particular responses by an animal, such as immune responses, inflammatory responses and allergic responses. Cells involved in an immune response can include, for example, B cells, T cells, macrophages, dendritic cells, natural killer cells and plasma cells. Cells involved in inflammatory responses can include, for example, basophils, mast cells, eosinophils, neutrophils and macrophages. Cells involved in allergic responses can include, for example mast cells, basophils, B cells, T cells and macrophages. Thus the predicted structure of these MIRR complexes may be used for drug design to obtain agonists/antagonists that modulates the functions of these proteins, thereby regulating these biological processes.

Receptor Tyrosine Kinases

In still another embodiment, the methods of the invention can be used to predict the 3-D structure of a receptor tyrosine kinase, at least the transmembrane portion(s) thereof. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., (1987) *Science* 238:1717-1720 and Lindberg and Hunter, (1990) *Mol. Cell. Biol.* 10:6316-6324). The functional domains of the kinase region of these three classes of receptor tyrosine kinases are encoded as a contiguous sequence (Hanks et al. (1988) *Science* 241:42-52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) *Science* 238:1717-1720), sequences have been reported for at least ten members of this family, not counting apparently orthologous receptors found in more than one species. Additional partial sequences, and the rate at which new members are still being reported, suggest the family is even larger (Maisonpierre et al. (1993) *Oncogene* 8:3277-3288; Andres et al. (1994) *Oncogene* 9:1461-1467; Henkemeyer et al. (1994) *Oncogene* 9:1001-1014; Ruiz et al. (1994) *Mech Dev* 46:87-100; Xu et al. (1994) *Development* 120:287-299; Zhou et al. (1994) *J Neurosci Res* 37:129-143; and references in Tuzi and Gullick (1994) *Br J Cancer* 69:417-421). Remarkably, despite the large number of members in the EPH family, all of these molecules were identified as orphan receptors without known ligands.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al. (1992) *Oncogene* 7:2499-2506; Nieto et al. (1992) *Development* 116:1137-1150; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in Drosophila, these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelial tissues, lung, pancreas, liver and kidney tissues. Observations such as this have been indicative of important and unique roles for EPH family kinases in development and physiology, but further progress in understanding their action has been severely limited by the lack of information on their ligands.

As used herein, the terms "EPH receptor" or "EPH-type receptor" refer to a class of receptor tyrosine kinases, comprising at least eleven paralogous genes, though many more orthologs exist within this class, e.g., homologs from different species. EPH receptors, in general, are a discrete group of receptors related by homology and easily recognizable, for example, they are typically characterized by an extracellular domain containing a characteristic spacing of cysteine residues near the N-terminus and two fibronectin type III repeats (Hirai et al. (1987) *Science* 238:1717-1720; Lindberg et al. (1990) *Mol Cell Biol* 10:6316-6324; Chan et al. (1991) *Oncogene* 6:1057-1061; Maisonpierre et al. (1993) *Oncogene* 8:3277-3288; Andres et al. (1994) *Oncogene* 9:1461-1467; Henkemeyer et al. (1994) *Oncogene* 9:1001-1014; Ruiz et al. (1994) *Mech Dev* 46:87-100; Xu et al. (1994) *Development* 120:287-299; Zhou et al. (1994) *J Neurosci Res* 37:129-143; and references in Tuzi and Gullick (1994) *Br J Cancer* 69:417-421). Exemplary EPH receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention.

Chemoattractant Receptors

The N-formyl peptide receptor is a classic example of a calcium mobilizing G protein-coupled receptor expressed by neutrophils and other phagocytic cells of the mammalian immune system (Snyderman et al. (1988) *In Inflammation: Basic Principles and Clinical Correlates*, pp. 309-323). N-Formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyogenic infections. Similar signal transduction occurs in response to the inflammatory peptides C5a and IL-8.

Two other formyl peptide receptor like (FPRL) genes have been cloned based on their ability to hybridize to a fragment of the NFPR cDNA coding sequence. These have been named FPRL1 (Murphy et al. (1992) *J. Biol Chem.* 267:7637-7643) and FPRL2 (Ye et al. (1992) *Biochem Biophys Res. Comm.* 184:582-589). FPRL2 was found to mediate calcium mobilization in mouse fibroblasts transfected with the gene and exposed to formyl peptide. In contrast, although FPRL1 was found to be 69% identical in amino acid sequence to NFPR, it did not bind prototype N-formyl peptides ligands when expressed in heterologous cell types. This leads to the hypothesis of the existence of an as yet unidentified ligand for the FPRL1 orphan receptor (Murphy et al. supra).

EXAMPLES

The example described below are for illustrative purpose only, and should not be construed to be limiting in any respect.

Example 1

Validation of the Method by Predicting TM Helices in Bovine Rhodopsin

We have used the TM2ndS algorithm for predicting the structure for about 10 very different GPCR classes (Vaidehi, N., W. B. Floriano, R. Trabanino, S. E. Hall, P. Freddolino, E. J. Choi, G. Zamanakos, and W. A. Goddard. 2002. Prediction of structure and function of G-protein-coupled receptors. Proc. Natl. Acad. Sci. USA. 99:12622-12627). In each case the predicted binding site and binding energy agrees well with available experimental data, providing some validation of the TM region prediction. However only for bovine rhodopsin can we make precise comparisons to experimental structures. We have also used TM2ndS to predict the TM regions and length of TM regions for membrane proteins for which crystal structure is available. Our predictions give 100% of the database as membrane proteins. The length of the TM regions is predicted to within 2 residues of the crystal structure on either carboxy or amino terminus.

The crystal structure of bovine rhodopsin (resolution, 2.80 Å) was downloaded from the protein structure database (PDB entry 1F88). The Hg ions, sugars, and waters were deleted from this structure. This crystal structure is missing 10 complete residues in loop regions and the side-chain atoms for 15 additional residues. We added the missing residues and side chains using WHATIF (Vriend, 1990, incorporated herein by reference). Then we added hydrogens to all the residues using the PolyGraf software.

FIG. 2 compares the predictions of TM regions for bovine rhodopsin to the TM regions as defined in the crystal structure paper (Palczewski, K., Kumasaka, T., Hori, T., Behnke, C., Motoshima, H., Fox, B., Trong, I., Teller, D., Okada, T., Stenkamp, R., Yamamoto, M., Miyano, M., (2000), *Science*, 289, 739-745). Upon conducting an analysis of the phi-psi angles using PROCHECK (Laskowski, R. A., MacArthur, M. W., Moss, D. S., Thornton, J. M., 1993, J. Appl. Cryst., 26,283-291), we found a slightly different helical assignment. Here we consider the experimental structure to be in an α-helix if $-37<\phi<-77$ and $-27<\psi<-67$. Those residues which fall outside this range are indicated in lowercase letters. The largest error in TM helical prediction is 5 residues at the C-terminal end of helix 5. This error may be corrected by an improved capping procedure in which residues near the ends of predictions are checked to be helix breakers and broken at those positions if the helix length remains above the 21 residue lower limit. The next largest error is 3 residues in the N-terminal end of helix 6. The rest of the errors are less than 3 residues. Thus, the predictions are found to agree well with the crystal structure. Detailed analysis of the prediction results are provided below.

For TM1, the TM2ndS prediction adds P at the start and H at the end. In a subsequent 3-D protein structure prediction using MembStruk3.5 (see U.S. Ser. No. 60/494,971, supra), the final structure (φ, ψ) for this P is (not-applicable [N-terminus], −43.6) and for this H is (−54.3, −32.4), whereas the values obtained in the crystal structure are (−44.3, −24.9) and (−72.5, 69.5), respectively. Since P and possibly H might be expected to break the helix, it is possible to modify the procedure to exclude such terminal P or H in the helix. In that case, the prediction would be exactly the same as the experimental data.

For TM2, the TM2ndS prediction adds HG at the end. In our final structure, the (φ, ψ) for this H and G are (−73.6, −80.9) and (−55.0, 148.8), whereas the values obtained in the crystal structure are (−74.2, 0.5) and (66.1, 9.0), respectively. The crystal structure article considered the H as part of the helix. Since HG could be expected to break the helix, it is possible to modify the procedure to exclude the terminal HG in the helix. In fact, the HG angles in our final structure fall outside our criteria for α-helicity as a result of the MembStruk optimization of the structure.

For TM3, the TM2ndS prediction misses the RYVVV (SEQ ID NO: 22) assigned in the crystal structure to the helix. Since the first and second V do not have (φ, ψ) in the usual range for α-helices, we consider that the VVV should be excluded. However, the polar character of RY leads TM2ndS to miss assigning them as part of the helix. The crystallographic (φ, ψ) values for R and Y residues are (−55.5, −63.8) and (−44.6, −56.3), whereas the values obtained in our final structure are (76.7, −51.4) and (−62.9, 119.2). It should be pointed out that the B-factors on the cytoplasmic end of the rhodopsin crystal structure are high in this region of the helix (PDB entry 1F88). This indicates that the helix is probably fluxional even when the receptor is not activated. Consequently caution should be used when comparing our predictions with the crystal structure at this end. Also, because the helices are translated to align hydrophobic centers in a later step of the procedure, this uncertainty in TM helical prediction may only lead to local errors in atomic structure.

For TM4, the TM2ndS prediction adds G at the end and misses N at the start. The crystallographic (4), for these N and G residues are (−43.5, −59.6) and (169.8, 5.4), whereas the values obtained in our final structure are (−93.9, 119.6) and (112.5, −118.4). Thus the predictions are fine even though the G and N were mis-assigned. It is possible to modify the procedure to exclude a terminal G.

Compared to the crystal structure assignment, the TM2ndS prediction for TM5 adds LVF at the end and misses N at the start. In addition the GQ at the end terminus in the crystal structure assignment have (4), 0) outside the range for α-helices. Thus the terminal GQLVF (SEQ ID NO: 23) in the TM2ndS predictions may be in error, the largest error of any of the predictions. The crystallographic (φ, ψ) for these N and LVF residues are (−69.3, −51.1), (−48.2, −36.7), (−39.6, −27.1), and (−58.0, −26.5), whereas the values obtained in our final structure are (−109.9, −162.4), (−55.1, −47.8), (−63.4, −59.0), and (−81.5, 59.3). The rhodopsin crystal structure has high B-factors for the intracellular end of TM5 (just as for helix 3), suggesting caution in making comparisons.

For TM6, the TM2ndS prediction adds H at the end and misses EVT at the start. The crystallographic (φ, ψ) values for these EVT and H residues are (−57.6, −53.0), (−54.1, −55.7), (−56.3, −52.3), and (−81.3, 48.8), whereas the values obtained in our final structure are (−74.4, 72.3), (−73.1, 130.8), (−16.9, −53.0), and (7.1, 87.7). Thus the predictions are fine despite the misassignments. We are considering modifying our procedure to exclude a terminal H. In fact, the H angles in our final structure fall outside our criteria for α-helicity as a result of the MembStruk optimization of the structure.

For TM7, the TM2ndS prediction adds P at the start and misses Y at the end. The crystallographic (φ, ψ) for the P and Y residues are (−30.2, −48.1) and (−46.0, −55.0), whereas the value for P obtained in our final structure is (−43.6, −23.2). Since the current MembStruk protocol does not model the structures of the C- and N-termini, we did include the Y in our structure. Thus the predictions are fine despite the misassignments. It is possible to modify the procedure to exclude a terminal P, but it is not obvious that a modified method would automatically include the Y. In fact, the P angles in the final 3-D MembStruk predicted structure fall outside our criteria for α-helicity as a result of the MembStruk optimization of the structure.

Overall, we consider that the predictions agree sufficiently well with the crystal structure to be useful in building them into the assembly. In addition, we can see several improvements in the capping procedure of TM2ndS that could have decreased the errors in predicting which residues near the ends are considered to be helix breakers for capping the TM helices. However, this article is meant to validate the procedure we have been applying to many systems. Thus, the overall procedure may be kept without modification on the basis of our only independent validation.

Example 2

GPCR Mining From the Genome

Using the TM2ndS module without the capping functionality, and in an automated fashion, we have searched the cDNA sequences in databases that are annotated to be proteins in the genome. The flowchart of this automated version of TM2ndS for data mining is shown in FIG. 3. Instead of applying a multiple sequence alignment on various sequences, one sequence was used for TM2ndS prediction (as on left side of flowchart). We used the cDNA sequences from the Riken database (J. Kawai, A. Shinagawa, et al. 2001, Nature, 409, 685-690) for this purpose, and the results for GPCR mining are given below.

The Riken Mouse Gene Encyclopedia Project was aimed at determining the function of a full cDNA library obtained for the Mouse genome. This is a good validation for the technique of data mining by searching (using TM2ndS without capping), sequences which potentially have the function of a G-protein coupled receptor. I infer function from structure, so I search for 7 helix proteins with TM2ndS.

Of the 20,000 clones we translated in all reading frames, 641 were found by the program to be putative 7 helix. This is about 3%, which has been estimated to be the percentage of GPCRs in all mouse proteome. The positive hits for GPCRs are shown in FIG. 4. It should be noted that these sequences are over 300 residues long, which is typical of a GPCR. The false negatives are shown in FIG. 5. It should be noted that these are all of size less than 250 residues, which points to possible fragmentation of these cDNA's and thus explains why TM2ndS did not find 7 helices in these cases.

Of the >20,000 clones obtained by the Riken database, only 361 were classified. Of these, only about 30-40 are classified as GPCRs. The other GPCRs are either missing from the library or are unclassified. Thus, TM2ndS was able to determine essentially all classified GPCRs from this database. In addition to this, other sequences which were found to be GPCRs may be orphan receptors (ligands and/or functions unknown). In fact, many sequences were classified as KIAA (potential GPCR in literature) and hypothetical proteins.

Their functions could be confirmed by either experiment or MembStruk/HierDock first principles procedures. In addition, false positives may be run through a second pass filter and largely eliminated.

This TM2ndS data mining procedure can be run on any generated cDNA clone library, or possible CDS genomes such as those from Celera or GENBANK® (genetic sequence database).

REFERENCES

1. Donnelly, D. (1993), *Biochem. Soc. T.* 21, 36-39.
2. Eisenberg D., Weiss R. M., Terwilliger, T. C., (1984), *Proc. Natl. Acad. Sci. USA*, 8, 140-144.
3. Donnelly, D., Overington, J. P. and Blundell, T. L. (1994) *Prot. Engin.* 7, 645-653.
4. Eisenberg, D., Weiss, R., Terwilliger, T., Wilcox, W. (1982) Faraday Symp. Chem. Soc., 17, 109-120.
5. Palczewski, K., Kumasaka, T., Hori, T., Behnke, C., Motoshima, H., Fox, B., Trong, I., Teller, D., Okada, T., Stenkamp, R., Yamamoto, M., Miyano, M., (2000), *Science*, 289, 739-745.
6. Laskowski, R. A., MacArthur, M. W., Moss, D. S., Thornton, J. M., 1993, J. Appl. Cryst., 26,283-291.
7. J. Kawai, A. Shinagawa, et al. 2001, Nature, 409, 685-690.
8. Altschul, S. F. Gish. W., Miller, W., Myers, E. W., and Lipman, D. J., Basic local alignment search tool. (1990) *J Mol Biol.*, 215, 403-410.
9. Altschul, S. F., Madden, T. L., Schaffer, A. A. Zhang, J., Zhang, Z., Miller, W. and Lipman D. J., (1997), *Nucleic Acids Res.* 25, 3389-3402. This computation was performed at the Swiss Institute of Bioinformatics using the BLAST network service.
10. Higgins, D., Thompson, J., Gibson, T., Thompson, J. D., Higgins, D. G., Gibson, T. J. (1994), *Nucleic Acids Res.* 22, 4673-4680.

The practice of the present invention will employ, unless otherwise indicated, conventional techniques of molecular biology, cell biology, cell culture, microbiology and recombinant DNA, which are within the skill of the art. Such techniques are explained fully in the literature. See, for example, *Molecular Cloning: A Laboratory Manual, $2^{nd}$ Ed.*, ed. By Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987).

The contents of all cited references (including literature references, issued patents, published patent applications as cited throughout this application) are hereby expressly incorporated by reference.

EQUIVALENTS

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

We claim:

1. A method for predicting the transmembrane (TM) region(s) of a TM protein, comprising:
   (1) obtaining amino acid sequence and/or sequence alignment for said TM protein;
   (2) plotting a hydrophobic profile using a specifically programmed computing device, and using said amino acid sequence and/or sequence alignment; and
   (3) assigning / identifying initial TM regions based on the global average hydrophobicity of said amino acid sequence and/or said sequence alignment, and a base_mod within 0.05 thereof;
   thereby predicting TM region(s) for said TM protein.

2. The method of claim 1, further comprising:
   (4) capping each initial TM regions identified in (3) to yield capped TM regions, based on the presence of helix breakers.

3. The method of claim 1, wherein said hydrophobic profile is based on at least a portion of said TM protein.

4. The method of claim 3, wherein said portion excludes one or more of: the N- or C-terminal region(s) not in contact with lipid bilayers, or inter-TM region loops.

5. The method of claim 1, wherein said hydrophobic profile uses peak signal analysis.

6. The method of claim 5, wherein said hydrophobic profile is generated by the SeqHyd profile algorithm.

7. The method of claim 6, comprising:
   (1) obtaining amino acid sequence and sequence alignment for said TM protein by:
      (a) using the sequence of said protein as query, retrieving from a database an ensemble of hit sequences with 20-90% sequence identity, and/or BLAST bit score >200 and E-value >$e^{-100}$;
      (b) obtaining a multisequence alignment of said hit sequences and the sequence of said protein; and
      (c) calculating consensus hydrophobicity for every residue position in said alignment;
   (2) plotting said hydrophobic profile based on said consensus hydrophobicity; and
   (3) assigning initial TM regions based on the global average hydrophobicity of said alignment, and a base_mod within 0.05 thereof.

8. The method of claim 7, further comprising:
   (4) capping each initial TM regions identified in (3) to yield capped TM regions, based on the presence of helix breakers.

9. The method of claim 7, wherein (3) further comprises identifying additional TM helix region(s) with peak length <23 and peak area <0.8, using local average hydrophobicity more than 0.05 less than said base_mod, if said additional TM helix region(s) are not identified based either on said global average hydrophobicity or said base_mod.

10. The method of claim 7, wherein said capped TM regions exclude N- and C-terminal helix breakers.

11. The method of claim 6, wherein said hydrophobic profile is based alone on the amino acid sequence of said protein.

12. The method of claim 11, comprising:
   (1) obtaining amino acid sequence for said TM protein;
   (2) plotting said hydrophobic profile based on the hydrophobicity of each residue within said amino acid sequence; and
   (3) assigning / identifying initial TM regions based on the global average hydrophobicity of said amino acid sequence alignment, and a base_mod within 0.05 thereof.

13. The method of claim 12, further comprising:
   (4) capping each initial TM regions identified in (3) to yield capped TM regions, based on the presence of helix breakers.

14. A non-transitory computer readable storage medium having a computer executable software code stored therein, which code, upon execution, carries out a method for predicting the transmembrane (TM) region(s) of a TM protein, said method comprising:
   (1) obtaining amino acid sequence and/or sequence alignment for said TM protein;
   (2) plotting a hydrophobic profile using said amino acid sequence and/or sequence alignment; and
   (3) assigning / identifying initial TM regions based on the global average hydrophobicity of said amino acid sequence and/or said sequence alignment, and a base_mod within 0.05 thereof;
   thereby predicting TM region(s) for said TM protein.

15. A computer hardware system for predicting the transmembrane (TM) region(s) of a TM protein, comprising:
   (1) a data input hardware module device for obtaining amino acid sequence and/or sequence alignment for said TM protein;
   (2) a profile generation hardware module device for plotting a hydrophobic profile using said amino acid sequence and/or sequence alignment; and
   (3) a TM region identification hardware module device for assigning / identifying initial TM regions based on the global average hydrophobicity of said amino acid sequence and/or said sequence alignment, and a base_mod within 0.05 thereof.

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Bos taurus

<400> SEQUENCE: 1

Glu Lys Glu Ala Tyr Ile His Leu
1               5

<210> SEQ ID NO 2
<211> LENGTH: 12
<212> TYPE: PRT
<213> ORGANISM: Bos taurus

<400> SEQUENCE: 2

Leu Met Leu Val Glu Glu Leu Cys Gly Ala Cys Ser
1               5                   10

<210> SEQ ID NO 3
<211> LENGTH: 10
<212> TYPE: PRT
<213> ORGANISM: Bos taurus

<400> SEQUENCE: 3

Arg Gly Asn Val Phe Glu Thr Met Cys Ile
1               5                   10
```

<210> SEQ ID NO 4
<211> LENGTH: 10
<212> TYPE: PRT
<213> ORGANISM: Bos taurus
<220> FEATURE:
<221> NAME/KEY: VARIANT
<222> LOCATION: 6, 9, 10
<223> OTHER INFORMATION: Xaa = Any Amino Acid

<400> SEQUENCE: 4

Phe Phe Ser Met Thr Xaa Asp Thr Xaa Xaa
1               5                   10

<210> SEQ ID NO 5
<211> LENGTH: 23
<212> TYPE: PRT
<213> ORGANISM: Bos taurus

<400> SEQUENCE: 5

Phe Ser Met Leu Ala Ala Tyr Met Phe Leu Leu Ile Met Leu Gly Phe
1               5                   10                  15

Pro Ile Asn Phe Leu Thr Leu
            20

<210> SEQ ID NO 6
<211> LENGTH: 32
<212> TYPE: PRT
<213> ORGANISM: Bos taurus

<400> SEQUENCE: 6

Pro Trp Gln Phe Ser Met Leu Ala Ala Tyr Met Phe Leu Leu Ile Met
1               5                   10                  15

Leu Gly Phe Pro Ile Asn Phe Leu Thr Leu Tyr Val Thr Val Gln His
            20                  25                  30

<210> SEQ ID NO 7
<211> LENGTH: 30
<212> TYPE: PRT
<213> ORGANISM: Bos taurus

<400> SEQUENCE: 7

Trp Gln Phe Ser Met Leu Ala Ala Tyr Met Phe Leu Leu Ile Met Leu
1               5                   10                  15

Gly Phe Pro Ile Asn Phe Leu Thr Leu Tyr Val Thr Val Gln
            20                  25                  30

<210> SEQ ID NO 8
<211> LENGTH: 28
<212> TYPE: PRT
<213> ORGANISM: Bos taurus

<400> SEQUENCE: 8

Leu Asn Leu Ala Val Ala Asp Leu Phe Met Val Phe Gly Gly Phe Thr
1               5                   10                  15

Thr Thr Leu Tyr Thr Ser Leu His Gly Tyr Phe Val
            20                  25

<210> SEQ ID NO 9
<211> LENGTH: 31
<212> TYPE: PRT
<213> ORGANISM: Bos taurus

<400> SEQUENCE: 9

```
Pro Leu Asn Tyr Ile Leu Leu Asn Leu Ala Val Ala Asp Leu Phe Met
1               5                   10                  15

Val Phe Gly Gly Phe Thr Thr Thr Leu Tyr Thr Ser Leu His Gly
            20                  25                  30
```

<210> SEQ ID NO 10
<211> LENGTH: 30
<212> TYPE: PRT
<213> ORGANISM: Bos taurus

<400> SEQUENCE: 10

```
Pro Leu Asn Tyr Ile Leu Leu Asn Leu Ala Val Ala Asp Leu Phe Met
1               5                   10                  15

Val Phe Gly Gly Phe Thr Thr Thr Leu Tyr Thr Ser Leu His
            20                  25                  30
```

<210> SEQ ID NO 11
<211> LENGTH: 31
<212> TYPE: PRT
<213> ORGANISM: Bos taurus

<400> SEQUENCE: 11

```
Val Phe Gly Pro Thr Gly Cys Asn Leu Glu Gly Phe Phe Ala Thr Leu
1               5                   10                  15

Gly Gly Glu Ile Ala Leu Trp Ser Leu Val Val Leu Ala Ile Glu
            20                  25                  30
```

<210> SEQ ID NO 12
<211> LENGTH: 28
<212> TYPE: PRT
<213> ORGANISM: Bos taurus

<400> SEQUENCE: 12

```
Pro Thr Gly Cys Asn Leu Glu Gly Phe Phe Ala Thr Leu Gly Gly Glu
1               5                   10                  15

Ile Ala Leu Trp Ser Leu Val Val Leu Ala Ile Glu
            20                  25
```

<210> SEQ ID NO 13
<211> LENGTH: 33
<212> TYPE: PRT
<213> ORGANISM: Bos taurus

<400> SEQUENCE: 13

```
Pro Thr Gly Cys Asn Leu Glu Gly Phe Phe Ala Thr Leu Gly Gly Glu
1               5                   10                  15

Ile Ala Leu Trp Ser Leu Val Val Leu Ala Ile Glu Arg Tyr Val Val
            20                  25                  30

Val
```

<210> SEQ ID NO 14
<211> LENGTH: 20
<212> TYPE: PRT
<213> ORGANISM: Bos taurus

<400> SEQUENCE: 14

```
Ile Met Gly Val Ala Phe Thr Trp Val Met Ala Leu Ala Cys Ala Ala
1               5                   10                  15

Pro Pro Leu Val
            20
```

<210> SEQ ID NO 15

```
<211> LENGTH: 23
<212> TYPE: PRT
<213> ORGANISM: Bos taurus

<400> SEQUENCE: 15

His Ala Ile Met Gly Val Ala Phe Thr Trp Val Met Ala Leu Ala Cys
 1               5                  10                  15

Ala Ala Pro Pro Leu Val Gly
            20

<210> SEQ ID NO 16
<211> LENGTH: 23
<212> TYPE: PRT
<213> ORGANISM: Bos taurus

<400> SEQUENCE: 16

Asn His Ala Ile Met Gly Val Ala Phe Thr Trp Val Met Ala Leu Ala
 1               5                  10                  15

Cys Ala Ala Pro Pro Leu Val
            20

<210> SEQ ID NO 17
<211> LENGTH: 25
<212> TYPE: PRT
<213> ORGANISM: Bos taurus

<400> SEQUENCE: 17

Val Ile Tyr Met Phe Val Val His Phe Ile Ile Pro Leu Ile Val Ile
 1               5                  10                  15

Phe Phe Cys Tyr Gly Gln Leu Val Phe
            20                  25

<210> SEQ ID NO 18
<211> LENGTH: 28
<212> TYPE: PRT
<213> ORGANISM: Bos taurus

<400> SEQUENCE: 18

Glu Ser Phe Val Ile Tyr Met Phe Val Val His Phe Ile Ile Pro Leu
 1               5                  10                  15

Ile Val Ile Phe Phe Cys Tyr Gly Gln Leu Val Phe
            20                  25

<210> SEQ ID NO 19
<211> LENGTH: 26
<212> TYPE: PRT
<213> ORGANISM: Bos taurus

<400> SEQUENCE: 19

Asn Glu Ser Phe Val Ile Tyr Met Phe Val Val His Phe Ile Ile Pro
 1               5                  10                  15

Leu Ile Val Ile Phe Phe Cys Tyr Gly Gln
            20                  25

<210> SEQ ID NO 20
<211> LENGTH: 20
<212> TYPE: PRT
<213> ORGANISM: Bos taurus

<400> SEQUENCE: 20

Ile Ile Met Val Ile Ala Phe Leu Ile Cys Trp Leu Pro Tyr Ala Gly
 1               5                  10                  15

Val Ala Phe Tyr
```

-continued

<210> SEQ ID NO 21
<211> LENGTH: 7
<212> TYPE: PRT
<213> ORGANISM: Bos taurus

<400> SEQUENCE: 21

Lys Thr Ser Ala Val Tyr Asn
 1               5

<210> SEQ ID NO 22
<211> LENGTH: 5
<212> TYPE: PRT
<213> ORGANISM: Bos taurus

<400> SEQUENCE: 22

Arg Tyr Val Val Val
 1               5

<210> SEQ ID NO 23
<211> LENGTH: 5
<212> TYPE: PRT
<213> ORGANISM: Bos taurus

<400> SEQUENCE: 23

Gly Gln Leu Val Phe
 1               5

<210> SEQ ID NO 24
<211> LENGTH: 27
<212> TYPE: PRT
<213> ORGANISM: Bos taurus

<400> SEQUENCE: 24

Arg Met Val Ile Ile Met Val Ile Ala Phe Leu Ile Cys Trp Leu Pro
 1               5                  10                  15

Tyr Ala Gly Val Ala Phe Tyr Ile Phe Thr His
            20                  25

<210> SEQ ID NO 25
<211> LENGTH: 31
<212> TYPE: PRT
<213> ORGANISM: Bos taurus

<400> SEQUENCE: 25

Glu Lys Glu Val Thr Arg Met Val Ile Ile Met Val Ile Ala Phe Leu
 1               5                  10                  15

Ile Cys Trp Leu Pro Tyr Ala Gly Val Ala Phe Tyr Ile Phe Thr
            20                  25                  30

<210> SEQ ID NO 26
<211> LENGTH: 21
<212> TYPE: PRT
<213> ORGANISM: Bos taurus

<400> SEQUENCE: 26

Pro Ile Phe Met Thr Ile Pro Ala Phe Phe Ala Lys Thr Ser Ala Val
 1               5                  10                  15

Tyr Asn Pro Val Ile
            20

<210> SEQ ID NO 27
<211> LENGTH: 21

```
-continued

<212> TYPE: PRT
<213> ORGANISM: Bos taurus

<400> SEQUENCE: 27

Ile Phe Met Thr Ile Pro Ala Phe Phe Ala Lys Thr Ser Ala Val Tyr
1               5                   10                  15

Asn Pro Val Ile Tyr
            20
```